(12) United States Patent
Nagy et al.

(10) Patent No.: US 12,110,519 B2
(45) Date of Patent: Oct. 8, 2024

(54) SPHERICAL AGGLOMERATION OF PROTEINS

(71) Applicant: Purdue Research Foundation, West Lafayette, IN (US)

(72) Inventors: Zoltan K. Nagy, West Lafayette, IN (US); Joseph A. Oliva, West Lafayette, IN (US); Kanjakha Pal, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 658 days.

(21) Appl. No.: 17/283,980

(22) PCT Filed: Oct. 2, 2019

(86) PCT No.: PCT/US2019/054241
§ 371 (c)(1),
(2) Date: Apr. 9, 2021

(87) PCT Pub. No.: WO2020/086227
PCT Pub. Date: Apr. 30, 2020

(65) Prior Publication Data
US 2021/0380959 A1    Dec. 9, 2021

Related U.S. Application Data

(60) Provisional application No. 62/751,878, filed on Oct. 29, 2018, provisional application No. 62/750,807, filed on Oct. 25, 2018.

(51) Int. Cl.
*C12N 9/36* (2006.01)
*A61K 38/47* (2006.01)
*C07K 1/02* (2006.01)
*C12N 9/98* (2006.01)

(52) U.S. Cl.
CPC ............ *C12N 9/2462* (2013.01); *A61K 38/47* (2013.01); *C07K 1/026* (2013.01); *C12N 9/98* (2013.01); *C12Y 302/01017* (2013.01)

(58) Field of Classification Search
None
See application file for complete search history.

(56) References Cited

U.S. PATENT DOCUMENTS

| 2002/0000681 A1 | 1/2002 | Gupta et al. |
| 2010/0228011 A1 | 9/2010 | Dong et al. |
| 2016/0250615 A1 | 9/2016 | Azevedo Ferreira et al. |

OTHER PUBLICATIONS

Yang, H. et al., Continuous protein crystallisation platform and process: Case of lysozyme, Jun. 5, 2018, Chem. Eng. Res. and Des., vol. 136, 529-535 (Year: 2018).*

(Continued)

*Primary Examiner* — Craig D Ricci
*Assistant Examiner* — Paul Hoerner
(74) *Attorney, Agent, or Firm* — Purdue Research Foundation

(57) ABSTRACT

The present disclosure relates to a novel spherical agglomeration method for proteins, and protein particles made by the spherical agglomeration method. By using continuous oscillatory baffled crystallizer, the method of the present disclosure is capable of maintain the biologically activities and providing protein particles with an average particle size between 1-500 μm.

2 Claims, 4 Drawing Sheets

(56) References Cited

OTHER PUBLICATIONS

Katta, J. et al., Spherical crystallization of benzoic acid, Jul. 10, 2007, Int. J. Pharma, VOl. 348, 61-69 (Year: 2007).*
Houen, G. The solubility of proteins in organic solvents, 1996, Acta Chemica Scandinavica, vol. 50, 68-70 (Year: 1996).*
International Search Report and Written Opinion, Jun. 1, 2020.
Lawton S., et al., Continuous Crystallization of Pharmaceuticals Using a Continuous Oscillatory Baffled Crystallizer, Organic Process Research & Development 2009, 13, 1357-1363.
Roberts M. M. et al., Protein Crystallization by Forced Flow through Glass Capillaries: Enhanced Lysozyme Crystal Growth, Crystal Growth & Design, vol. 10, No. 3, 2010, 1075.
Pena R., et al., Process Intensification through Continuous Spherical Crystallization Using an Oscillatory Flow Baffled Crystallizer, Cryst. Growth Des. 2017, 17, 4776-4784.
Zhang X., et al., The study of continuous membrane crystallization on lysozyme, Desalination 219 (2008) 101-117.

\* cited by examiner

U = 1 micro mol of product per minute at pH 5.0, 37 C

SPHERICAL AGGLOMERATION OF PROTEINS

CROSS-REFERENCE TO RELATED APPLICATION

This application is a national stage entry under 35 U.S.C. § 371 (b) of International Application No. PCT/US19/54241, filed Oct. 2, 2019, which claims the priority benefit of U.S. Provisional Application No. 62/750,807, filed Oct. 25, 2018, and 62/751,878, filed Oct. 29, 2018, the contents of which are hereby incorporated by reference in their entireties.

TECHNICAL FIELD

The present disclosure relates to a novel spherical agglomeration method for proteins, and protein particles made by the spherical agglomeration method.

BACKGROUND

This section introduces aspects that may help facilitate a better understanding of the disclosure. Accordingly, these statements are to be read in this light and are not to be understood as admissions about what is or is not prior art.

The industrial crystallization of proteins typically occurs on the order of 10 hour batch times and then requires a freeze drying operation to isolate the purified product. The resulting proteins may have poor macroscopic flowability and aggregates uncontrollably during the freeze drying step.

Therefore, there is an unmet need for a better and controllable method to prepare protein particles with improved production, flowability, and stability.

To overcome this bottleneck in product purification and isolation, the proposed work aims to tailor the overall particle size by controlling the agglomeration mechanism instead of focusing on the growth kinetics during crystallization.

SUMMARY

The present disclosure relates to a novel spherical agglomeration method for proteins, and protein particles made by the spherical agglomeration method.

In one embodiment, the present disclosure provides a novel spherical agglomeration method for proteins, wherein the method comprises:
  a) dissolving a protein in water to prepare a aqueous solution of the protein;
  b) providing an organic solvent mixture comprising a first organic solvent as a poor solvent for the protein and a second organic solvent as a good solvent for the protein;
  c) providing a continuous oscillatory baffled crystallizer with an inlet and an outlet, and allowing the organic solvent mixture to run from the inlet of the continuous oscillatory baffled crystallizer and out form the outlet the organic solvent mixture; and
  d) injecting the aqueous solution of the protein through a middle point of the continuous oscillatory baffled crystallizer to allow the formation of protein crystals, wherein the crystals agglomerate to form substantially spherical protein particles toward the outlet of the continuous oscillatory baffled crystallizer.

DETAILED DESCRIPTION

Figure 1:
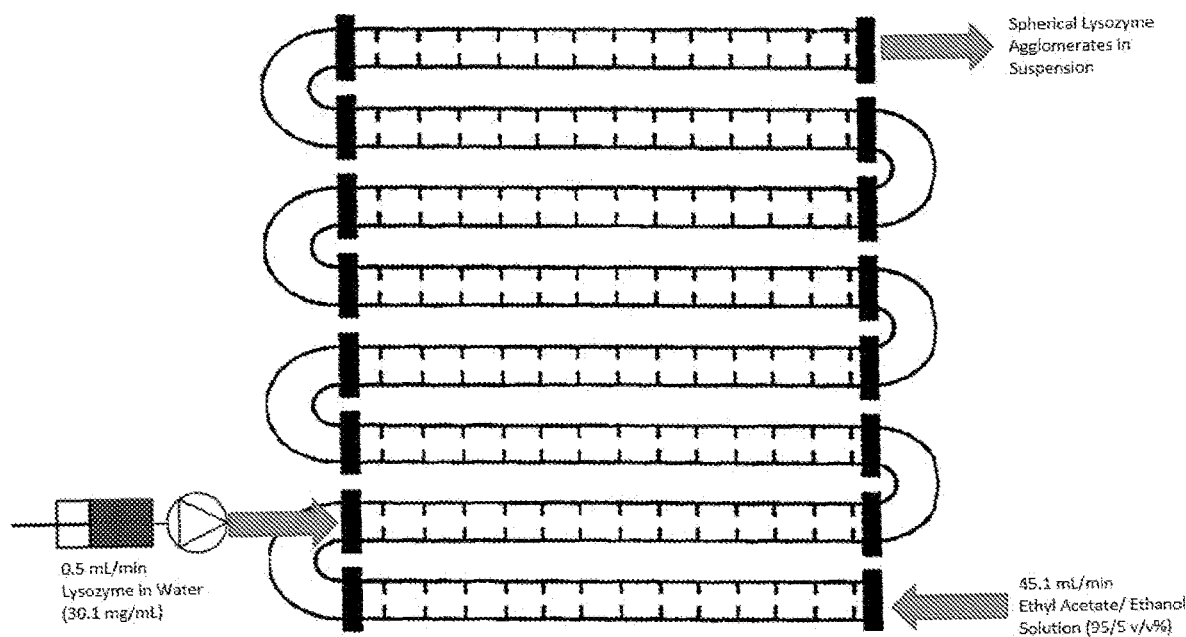
FIG. 1 shows the experimental setup of a spherical agglomeration system.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

In the present disclosure the term "about" can allow for a degree of variability in a value or range, for example, within 10%, within 5%, or within 1% of a stated value or of a stated limit of a range.

In the present disclosure the term "substantially" can allow for a degree of variability in a value or range, for example, within 90%, within 95%, or within 99% of a stated value or of a stated limit of a range.

In the present disclosure the term "solvent" refers to most low toxicity solvents such as class 3 solvents including but is not limited to acetic acid, acetone, anisole, 1-butanol, 2-butanol, butyl acetate, tert-butylmethyl ether, cumene, dimethyl sulfoxide, ethanol, ethyl acetate, ethyl ether, ethyl formate, formic acid, heptane, isobutyl acetate, isopropyl acetate, methyl acetate, 3-methyl-1-butanol, methylethyl ketone, methylisobutyl ketone, 2-methyl-1-propanol, pentane, 1-pentanol, 1-propanol, 2-propanol, propyl acetate, tetrahydrofuran, or any combination thereof.

In the present disclosure the term "poor solvent" means that a solvent can only dissolve a protein with a solubility of equal or less than 0.1 mg/mL, or 0.05 mg/mL at room temperature, at a pH that the protein can maintain biological activity.

In the present disclosure the term "good solvent" means that a solvent can dissolve a protein with a solubility of equal or more than 10 mg/mL, 20 mg/mL, or 30 mg/mL at room temperature, at a pH that the protein can maintain biological activity.

In the present disclosure the term "flowable or flowability" means that most protein particles are not stick together, and can flow freely. The higher flowability may also help the filtration of the protein particles from a protein particle suspension.

In the present disclosure the term "protein" means any possible bioactive proteins such as enzymes, polyclonal or monoclonal antibodies (mAbs).

The industrial crystallization of proteins such as lysozyme typically occurs on the order of about 10 hour batch times and then requires a freeze drying operation to isolate the purified product. The resulting lysozyme has poor macroscopic flowability and aggregates uncontrollably during the freeze drying step. To overcome this bottleneck in product purification and isolation, the proposed work aims to tailor the overall particle size by controlling the agglomeration mechanism instead of focusing on the growth kinetics during crystallization.

Using a continuous oscillatory baffled crystallizer (COBC), lysozyme crystals can be generated through the suspension of immiscible solvent droplets. Water is immiscible with ethyl acetate (the bulk solution) and contains dissolved lysozyme before being added dropwise to the system via the incorporation of a syringe pump. The solubility of lysozyme in water at room temperature is on the order of 100 mg/mL (pH=4) and the solubility of lysozyme in ethyl acetate at room temperature is <0.05 mg/mL. Exterior to the water droplet, as the ethyl acetate/ethanol solution enters the droplet via counter-diffusion and high mixing intensity, the newly formed lysozyme crystals tend to agglomerate very quickly due to the highly unfavorable environment. As a result, by controlling the oscillatory mixing conditions in the crystallizer as well as the droplet size, the size of the agglomerates can be tailored to form free flowing, compact spheres on the order of minutes instead of hours.

Figure 2:
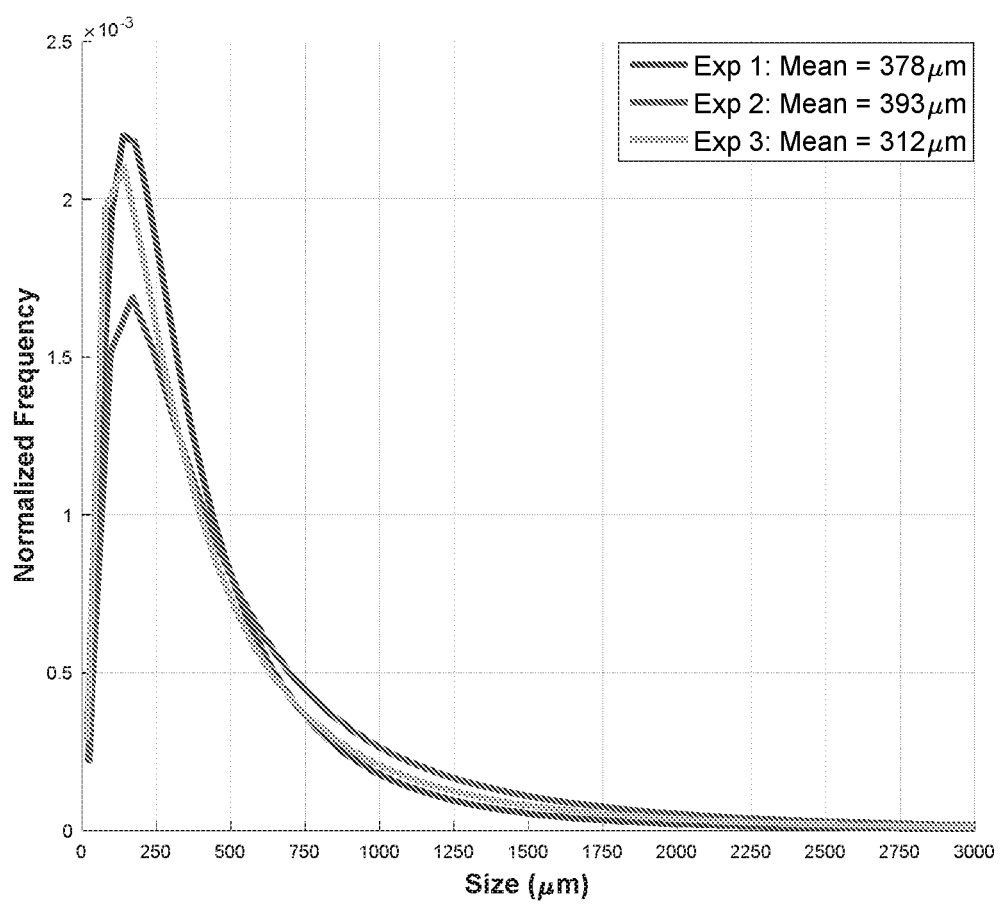
FIG. 2 shows agglomerate size distribution of lysozyme as a function of protein injection rate.

Using the conditions mentioned in FIG. 1 while operating at an oscillation amplitude and frequency of 15 mm and 2 Hz respectively (residence time=27.4 min), lysozyme spheres were produced at a rate of roughly 20 g/day. A small sensitivity analysis was carried out to determine the effect of lysozyme flow rate on overall particle size. As described in FIG. 2, the mean size of the lysozyme agglomerates is relatively constant as a function of injection rate. This result suggests that the size of the agglomerates formed may be a function of the droplet size. In FIG. 2, the flow rate of lysozyme solution (mL/min) in Exp. 1, 2, and 3 are 0.5, 0.75, and 1.0, respectively.

Figure 3:
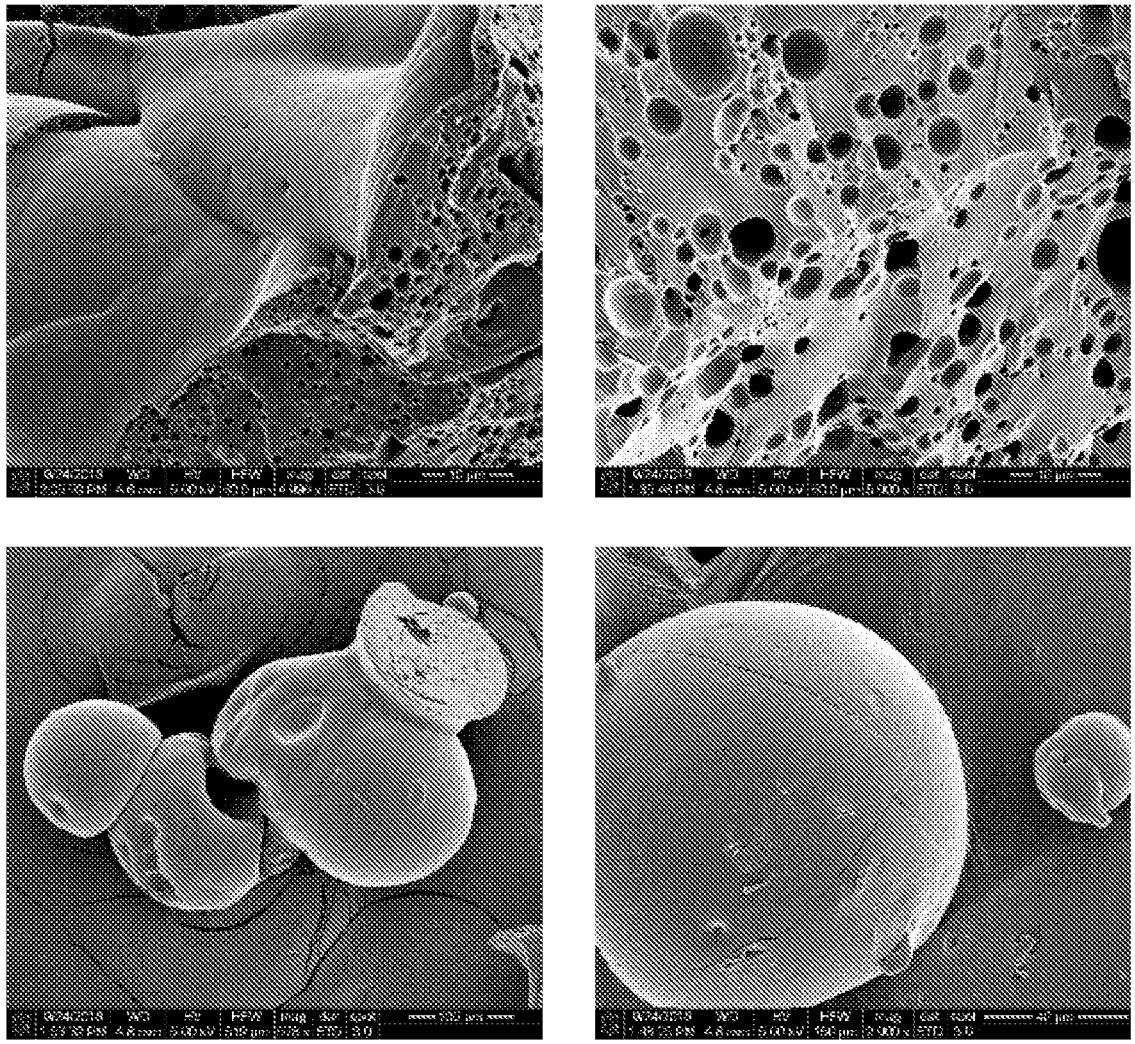
FIG. 3 shows (top) SEM images taken using slices of spherical lysozyme agglomerates, (bottom) whole lysozyme agglomerates with some evidence of coalescence.

Using a scanning electron microscope, detailed images of the product generated from Exp. 1 were taken. Certain images were selected and are shown in FIG. 3. From the top two images, it is clear that the spheres are in fact porous, likely due to rapid nucleation/agglomeration kinetics. As these mechanisms take place, solvent is squeezed out of the protein, leaving voids behind. From the images in the bottom of FIG. 3, the outside of the agglomerate is seen to be very smooth. This result is likely due to the agitation inside of the reactor. With vigorous mixing, the outside of the sphere is smoothed via a surface layering mechanism, covering the outermost pores with deposited protein. This porous material property may prove useful for enhanced dissolution kinetics and drug excipient loading applications.

Figure 4:
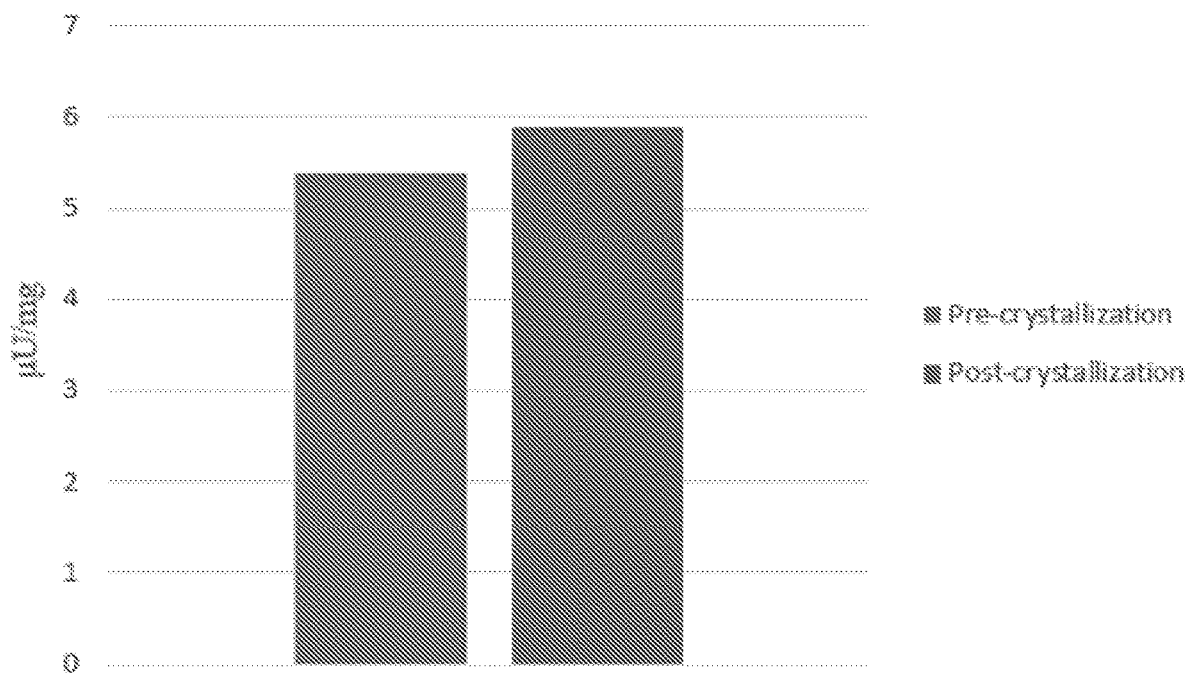
FIG. 4 shows the enzyme activity for lysozyme particles before and after the spherical agglomeration.

In the spherical agglomeration process for enzymes/proteins, it is critical to maintain the enzyme activity for the particles obtained because certain organic solvents may impact the protein/enzyme activities. However, it is unexpectedly found that the particles obtained may have even better activity. FIG. 4 demonstrated that the lysozyme flowable particles with average particle size around 300-400 μm obtained through spherical agglomeration method had even better activities.

From the aforementioned results, lysozyme spheres were produced with enhanced micromeritic flow properties in roughly $1/20^{th}$ of the time required by traditional batch processing. To improve production per day at the lab scale, additional parameter sensitivity analysis is required including droplet concentration, droplet size, and residence time. These enhanced material properties each have important implications including improved shelf life, transportability, and compatibility.

In one embodiment, the protein particles obtained with the method in the present disclosure maintains the biological activities at least to about 60%, 70%, 80%, 90%, 95%, 96%, 97%, 98%, 99%, 100% of the biological activities of the same currently available commercial protein with less flowable and smaller particles. In one aspect, the protein particles obtained with the method in the present disclosure may have better biological activities. In one aspect, the protein is lysozyme.

In one embodiment, the protein particles obtained with the method in the present disclosure have an average particle size range of about 1 to 1000 μm, 1 to 750 μm, 1 to 500 μm, 1 to 400 μm, 1 to 300 μm, 1 to 200 μm, 1 to 100 μm, 50 to 1000 μm, 50 to 750 μm, 50 to 500 μm, 50 to 400 μm, 50 to 300 μm, 50 to 200 μm, 50 to 100 μm, 100 to 1000 μm, 100 to 750 μm, 100 to 500 μm, 100 to 400 μm, 100 to 300 μm, 100 to 200 μm, or any combination thereof.

Those skilled in the art will recognize that numerous modifications can be made to the specific implementations described above. The implementations should not be limited to the particular limitations described. Other implementations may be possible.

We claim:

1. A method for making spherical protein particles, wherein the method comprises:
   a) dissolving a protein in water to prepare an aqueous solution of the protein;
   b) providing an organic solvent mixture comprising a first organic solvent, which is immiscible with water, and a second organic solvent, which is miscible with water;
   c) providing a continuous oscillatory baffled crystallizer with an inlet and an outlet, and allowing the organic solvent mixture to run from the inlet of the continuous oscillatory baffled crystallizer and out from the outlet of the continuous oscillatory baffled crystallizer;
   d) injecting the aqueous solution of the protein dropwise through a point between the inlet and the outlet of the continuous oscillatory baffled crystallizer to form droplets of the aqueous protein solution, whereupon the second organic solvent diffuses into the droplets of the aqueous protein solution and the first organic solvent suspends the droplets of the aqueous protein solution; and
   e) allowing a formation of protein crystals, wherein the formed protein crystals agglomerate to form substantially spherical protein particles towards the outlet of the continuous oscillatory baffled crystallizer,
   wherein the protein is lysozyme, the first organic solvent is ethyl acetate, and the second organic solvent is ethanol.

2. The method of claim 1, wherein the ethyl acetate and the ethanol are present in the ratio of about 95:5% v/v.

* * * * *